United States Patent
Foley et al.

(10) Patent No.: US 6,434,415 B1
(45) Date of Patent: *Aug. 13, 2002

(54) SYSTEM FOR USE IN DISPLAYING IMAGES OF A BODY PART

(75) Inventors: Kevin T. Foley, Germantown, TN (US); Richard D. Bucholz, St. Louis, MO (US); Kurt R. Smith, Boulder, CO (US)

(73) Assignees: St. Louis University, St. Louis, MO (US); Surgical Navigation Technologies, Inc., Louisville, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/398,313

(22) Filed: Sep. 20, 1999

Related U.S. Application Data

(63) Continuation of application No. 08/931,654, filed on Sep. 16, 1997, now Pat. No. 6,347,240, which is a continuation of application No. 08/319,615, filed on Oct. 7, 1994, now abandoned, which is a continuation-in-part of application No. 08/053,076, filed on Apr. 26, 1993, now abandoned, which is a continuation-in-part of application No. 07/909,097, filed on Jul. 2, 1992, now Pat. No. 5,383,454, which is a continuation of application No. 07/600,753, filed on Oct. 19, 1990, now abandoned.

(51) Int. Cl.$^7$ ................................................ A61B 6/00
(52) U.S. Cl. ................... 600/425; 600/427; 600/429; 600/437; 606/130
(58) Field of Search ................ 600/407, 410, 600/414, 415, 417, 425, 426, 427, 429, 437; 606/130

(56) References Cited

U.S. PATENT DOCUMENTS

| 3,821,469 A | 6/1974 | Whetstone |
| 3,868,565 A | 2/1975 | Kulpers |

(List continued on next page.)

FOREIGN PATENT DOCUMENTS

| DE | 2534516 | 2/1976 |
| DE | 2852949 | 6/1980 |
| DE | 3205085 | 9/1982 |
| DE | 3508730 | 9/1986 |
| DE | 8701668 | 5/1987 |

(List continued on next page.)

OTHER PUBLICATIONS

Adams, et al., "Computer–Assisted Surgery," Medical Imaging, *IEEE*, pp. 43–51, (May 1990).

(List continued on next page.)

*Primary Examiner*—Ruth S. Smith
(74) *Attorney, Agent, or Firm*—Senniger, Powers, Leavitt & Roedel

(57) ABSTRACT

A system for use during a medical or surgical procedure on a body. The system generates a display representing the position of two or more body elements during the procedure based on an image data set generated by a scanner prior to the procedure. The image data set has reference points for each of the body elements, the reference points of a particular body element having a fixed spatial relation to the particular body element. The system includes an apparatus for identifying, during the procedure, the relative position of each of the reference points of each of the body elements to be displayed. The system also includes a processor for modifying the image data set according to the identified relative position of each of the reference points during the procedure, as identified by the identifying apparatus, said processor generating a displaced image data set representing the position of the body elements during the procedure. The system also includes a display utilizing the displaced image data set generated by the processor, illustrating the relative position of the body elements during the procedure. Methods relating to the system are also disclosed.

25 Claims, 11 Drawing Sheets

U.S. PATENT DOCUMENTS

| | | |
|---|---|---|
| 3,963,028 A | 6/1976 | Cooley et al. |
| 3,983,474 A | 9/1976 | Kuipers |
| 4,058,114 A | 11/1977 | Soldner |
| 4,068,156 A | 1/1978 | Johnson et al. |
| 4,117,337 A | 9/1978 | Staats |
| 4,182,312 A | 1/1980 | Mushabac |
| 4,209,254 A | 6/1980 | Reymond |
| 4,259,725 A | 3/1981 | Andrews et al. |
| 4,341,220 A | 7/1982 | Perry |
| 4,358,856 A | 11/1982 | Stivender et al. |
| 4,368,556 A | 1/1983 | Wanner et al. |
| 4,396,945 A | 8/1983 | DiMatteo et al. |
| 4,398,540 A | 8/1983 | Takemura et al. |
| 4,407,298 A | 10/1983 | Lentz et al. |
| 4,419,012 A | 12/1983 | Stephenson |
| 4,457,311 A | 7/1984 | Sorenson et al. |
| 4,465,069 A | 8/1984 | Barbler et al. |
| 4,473,074 A | 9/1984 | Vassiliadis |
| 4,506,676 A | 3/1985 | Duska |
| 4,543,959 A | 10/1985 | Sepponen |
| 4,571,834 A | 2/1986 | Fraiser et al. |
| 4,583,538 A | 4/1986 | Onik et al. |
| 4,585,350 A | 4/1986 | Pryer et al. |
| 4,592,352 A | 6/1986 | Patil |
| 4,602,622 A | 7/1986 | Bar et al. |
| 4,608,977 A | 9/1986 | Brown |
| 4,638,798 A | 1/1987 | Sheldon et al. |
| 4,649,504 A | 3/1987 | Krouglicof et al. |
| 4,651,732 A | 3/1987 | Frederick |
| 4,659,971 A | 4/1987 | Suzuki et al. |
| 4,660,970 A | 4/1987 | Ferrano |
| 4,672,306 A | 6/1987 | Thong |
| 4,673,352 A | 6/1987 | Hansen |
| 4,674,057 A | 6/1987 | Caughman et al. |
| D291,246 S | 8/1987 | Lower |
| 4,686,997 A | 8/1987 | Oloff et al. |
| 4,698,777 A | 10/1987 | Toyoda et al. |
| 4,701,047 A | 10/1987 | Eibert et al. |
| 4,701,049 A | 10/1987 | Beckmann |
| 4,701,407 A | 10/1987 | Seppel |
| 4,705,395 A | 11/1987 | Hageniers |
| 4,705,401 A | 11/1987 | Addleman |
| 4,706,665 A | 11/1987 | Gouda |
| 4,709,156 A | 11/1987 | Murphy |
| 4,721,384 A | 1/1988 | Dietrich et al. |
| 4,721,388 A | 1/1988 | Takagi et al. |
| 4,722,056 A | 1/1988 | Roberts et al. |
| 4,723,544 A | 2/1988 | Moore et al. |
| 4,727,565 A | 2/1988 | Ericson |
| 4,733,661 A | 3/1988 | Palestrant |
| 4,733,662 A | 3/1988 | DeSatnick |
| 4,733,969 A | 3/1988 | Case et al. |
| 4,737,032 A | 4/1988 | Addleman et al. |
| 4,737,921 A | 4/1988 | Goldwasser et al. |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,128 A | 6/1988 | Bartlett et al. |
| 4,753,528 A | 6/1988 | Hines |
| 4,761,072 A | 8/1988 | Pryor |
| 4,762,016 A | 8/1988 | Stoughton et al. |
| 4,764,015 A | 8/1988 | Bieringer et al. |
| 4,764,016 A | 8/1988 | Johanasson |
| 4,767,934 A | 8/1988 | Stauffer |
| 4,771,787 A | 9/1988 | Wurster et al. |
| 4,775,235 A | 10/1988 | Hecker et al. |
| 4,776,749 A | 10/1988 | Wanzenberg et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunett |
| 4,793,355 A | 12/1988 | Crum et al. |
| 4,794,262 A | 12/1988 | Sato et al. |
| 4,803,645 A | 2/1989 | Ohtomo et al. |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,822,163 A | 4/1989 | Schmidt |
| 4,825,091 A | 4/1989 | Breyer et al. |
| 4,829,373 A | 5/1989 | Leberl et al. |
| 4,835,710 A | 5/1989 | Schnelle et al. |
| 4,836,778 A | 6/1989 | Baumrind et al. |
| 4,837,669 A | 6/1989 | Tharp et al. |
| 4,841,967 A | 6/1989 | Chang et al. |
| 4,875,478 A | 10/1989 | Chen |
| 4,896,673 A | 1/1990 | Rose et al. |
| 4,931,056 A | 6/1990 | Ghajar et al. |
| 4,933,843 A | 6/1990 | Scheller et al. |
| 4,943,296 A | 7/1990 | Funakubo et al. |
| 4,945,914 A | 8/1990 | Allen |
| 4,955,891 A | 9/1990 | Carol |
| 4,961,422 A | 10/1990 | Marchosky |
| 4,982,188 A | 1/1991 | Fodale et al. |
| 4,991,579 A | 2/1991 | Allen |
| 5,005,142 A | 4/1991 | Lipchak et al. |
| 5,016,639 A | 5/1991 | Allen |
| 5,017,139 A | 5/1991 | Mushabac |
| 5,027,810 A | 7/1991 | Bova et al. |
| 5,039,867 A | 8/1991 | Nishihara et al. |
| 5,047,036 A | 9/1991 | Koutrouvelis |
| 5,050,608 A | 9/1991 | Watanabe et al. |
| 5,059,789 A | 10/1991 | Salcudean et al. |
| 5,078,140 A | 1/1992 | Kwoh |
| 5,078,142 A | 1/1992 | Scizek et al. |
| 5,079,699 A | 1/1992 | Tuy et al. |
| 5,080,662 A | 1/1992 | Paul |
| 5,086,401 A | 2/1992 | Glassman et al. |
| 5,094,241 A | 3/1992 | Allen |
| 5,097,839 A | 3/1992 | Allan |
| 5,099,846 A | 3/1992 | Hardy |
| 5,107,839 A | 4/1992 | Houdek et al. |
| 5,119,817 A | 6/1992 | Allen |
| 5,142,930 A | 9/1992 | Allen et al. |
| 5,178,164 A | 1/1993 | Allen |
| 5,186,174 A | 2/1993 | Schlondorff et al. |
| 5,193,106 A | 3/1993 | DeSena |
| 5,197,476 A | 3/1993 | Nowacki et al. |
| 5,207,223 A | 5/1993 | Adler |
| 5,211,164 A | 5/1993 | Allen |
| 5,222,499 A | 6/1993 | Allen et al. |
| 5,224,049 A | 6/1993 | Mushabac |
| 5,230,338 A | 7/1993 | Allen et al. |
| 5,249,581 A | 10/1993 | Horbal et al. |
| 5,251,127 A | 10/1993 | Raab |
| 5,257,998 A | 11/1993 | Ota et al. |
| 5,261,404 A | 11/1993 | Mick et al. |
| 5,279,309 A | 1/1994 | Taylor et al. |
| 5,291,889 A | 3/1994 | Kenet et al. |
| 5,295,200 A | 3/1994 | Boyer |
| 5,295,483 A | 3/1994 | Nowacki et al. |
| 5,299,288 A | 3/1994 | Glassman et al. |
| 5,305,091 A | 4/1994 | Gelbart et al. |
| 5,305,203 A | 4/1994 | Raab |
| 5,309,913 A | 5/1994 | Kormos et al. |
| D349,573 S | 8/1994 | Bookwalter |
| 5,355,129 A | 10/1994 | Baumann |
| 5,357,953 A | 10/1994 | Merrick et al. |
| 5,359,417 A | 10/1994 | Müller et al. |

| | | |
|---|---|---|
| 5,368,030 A | 11/1994 | Zinreich et al. |
| D353,668 S | 12/1994 | Banks |
| 5,371,778 A | 12/1994 | Yanof et al. |
| 5,383,454 A | 1/1995 | Bucholz |
| 5,389,101 A | 2/1995 | Heilbrun et al. |
| 5,391,199 A | 2/1995 | Ben-Haim |
| 5,398,684 A | 3/1995 | Hardy |
| 5,399,146 A | 3/1995 | Nowacki et al. |
| 5,399,951 A | 3/1995 | Lavallee et al. |
| D357,534 S | 4/1995 | Hayes |
| D359,557 S | 6/1995 | Hayes |
| 5,443,489 A | 8/1995 | Ben-Haim |
| 5,447,154 A | 9/1995 | Cinquin et al. |
| 5,480,422 A | 1/1996 | Ben-Haim |
| 5,483,961 A | 1/1996 | Kelly et al. |
| 5,490,196 A | 2/1996 | Rudich et al. |
| 5,494,034 A | 2/1996 | Schlöndorff et al. |
| 5,515,160 A | 5/1996 | Schulz et al. |
| 5,517,990 A | 5/1996 | Kalfas et al. |
| 5,526,576 A | 6/1996 | Fuchs et al. |
| 5,531,227 A | 7/1996 | Schneider |
| 5,531,520 A | 7/1996 | Grimson et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,568,809 A | 10/1996 | Ben-Haim |
| 5,583,454 A | 12/1996 | Bucholz |
| 5,603,318 A | 2/1997 | Heilbrun et al. |
| 5,622,170 A | 4/1997 | Schultz |
| 5,638,819 A | 6/1997 | Manwaring et al. |
| 5,647,361 A | 7/1997 | Damadian |
| 5,662,111 A | 9/1997 | Cosman |
| 5,676,673 A | 10/1997 | Ferre et al. |
| 5,682,886 A | 11/1997 | Delp et al. |
| 5,728,106 A | 3/1998 | Misko et al. |
| 5,732,703 A | 3/1998 | Kalfas et al. |
| 6,236,875 B1 * | 5/2001 | Bucholz et al. ............. 600/407 |

FOREIGN PATENT DOCUMENTS

| | | | |
|---|---|---|---|
| DE | 3205915 | 9/1993 | |
| DE | 4432890 | 3/1996 | |
| EP | 0 018 166 | 4/1980 | |
| EP | 0 062 941 | 10/1982 | |
| EP | 0 155 857 | 1/1985 | |
| EP | 0 207 452 | 1/1987 | |
| EP | 0 322 363 | 6/1989 | |
| EP | 0 427 358 | 10/1990 | |
| EP | 0 456 103 | 5/1991 | |
| EP | 0 469 966 | 2/1992 | |
| EP | 0 359 773 | 10/1993 | |
| EP | 0 581 704 | 2/1994 | |
| EP | 0 603 089 | 6/1994 | |
| EP | 0 501 993 | 5/1996 | |
| EP | 0 326 768 | 12/1998 | |
| FR | 2 417 970 | 10/1979 | |
| GB | 2094590 | 2/1982 | |
| JP | 62-000327 | 1/1987 | |
| WO | WO 88/09151 | 12/1988 | |
| WO | WO 90/05494 | 5/1990 | |
| WO | WO 91/04711 | 4/1991 | |
| WO | WO 91/07726 | 5/1991 | |
| WO | WO 92/00702 | 7/1991 | |
| WO | WO 92/06645 | 10/1991 | |
| WO | WO 93/10710 | 6/1993 | |
| WO | WO 93/2052 | 10/1993 | |
| WO | WO 94/06352 | 3/1994 | |
| WO | WO 96/11624 | * 4/1996 | ................. 600/407 |

OTHER PUBLICATIONS

Adams et al., "Aide Au Reperage Tridimensional Pour La Chirurgie De La Base Du Crane," *Innov. Tech. Biol. Med.*, vol. 13, No. 4, pp. 409–424 (1992).

Afshar, Farhad, et al., "A three–dimensional reconstruction of the human brain stem," *J. Neurosurg.*, vol. 57, Oct. 1982, pp. 491–495.

Apuzzo, M.L.J., et al., "Computed tomographic Guidance Guidance Stereotaxis in the Management of Intracranial Mass Lesions," (1983).

Arun, K.S., et al., "Transactions on Pattern Analysis and Machine Intelligence," *IEEE*, vol. PAMI–9, No. 5, 1987, pp. 698–770.

Awwad, E.E., et al., "MR Imaging of Lumbar Juxtaarticular Cysts," *Journal of Computer Assisted Tomography*, vol. 14, No. 3, pp. 415–417, May/Jun. 1990.

Awwad, E.E., et al., "Post–Traumatic Spinal Synovial Cyst with Spondylolysis CT Features," *Journal of Computer Assisted Tomography*, vol. 13, No. 2, pp. 334–337, Mar./Apr. 1989.

Bajcsy, Ruzena, et al., "Computerized Anantomy Atlas of the Human Brain," Proceedings of the Second Annual Conference & Exhibition of the National Computer Graphics Association, Inc., Jun. 14–18, 1981, pp. 435–441.

Balter, James M., et al., "Correlation of projection radiographs in radiation therapy using open curve segments and points," *Med. Phys.* 19(2), Mar./Apr. 1992, pp. 329–334.

Batnitzky, Solomon, M.D., et al., "Three–Dimensional Computer Reconstructions of Brain Lesions from Surface Contours Provided by Computed Tomography: A Prospectus," *Neurosurgery*, vol. 11, No. 1, 1982, pp. 73–84.

Benzel, E.C., et al., "Magnetic Source Imaging: A Review of the Magnes System of Biomagnetic Technologies Incorporated," *Neurosurgery*, vol. 33, No. 2, pp. 252–259, Aug. 1993.

Bergström, Mats, et al., "Stereotaxic Computed Tomography," *Am. J. Roentgenol*, 127:167–170, 1976, pp. 167–170.

Birg, W., et al., "A Computer Programme System for Stereotactic Neurosurgery," *Acta Neurochirurgica Suppl.*, 24, 1977, 99–108.

Boëthius, J., et al., "Stereotaxic computerized tomography with a GE 8800 scanner," *J. Neurosurg.*, vol. 52, 1980, pp. 794–800.

Boëthius, J., et al., "Stereotactic Biopsies and Computer Tomography in Gliomas," *Acta Neurochirurgica*, vol. 40, Fasc. 3–4, 1978, pp. 223–232.

Brown, Russell A., M.D., "A computerized tomography–computer graphics approach to stereotaxic localization," *J. Neurosurg.*, vol. 50, 1979, pp. 715–720.

Brown, Russell A., "Stereotactic Head Frame for Use with CT Body Scanners," *Inv. Radiol.*, vol. 14, No. 4, pp. 300–304, Jul. 1979.

Bucholz, R.D., "The Central Sulcus and Surgical Planning," *AJNR*, vol. 14, pp. 929–7, Jul./Aug. 1993.

Bucholz, R.D., Declaration of Richard D. Bucholz, pp. 1–4, with attached Exhibits A (pp. 1–29) and B (p. 1–2), Dec. 2,3 1997.

Bucholz, R.D., et al., "Intraoperative Localization using a Three Dimensional Optical Digitizer," *Proceedings of Clinical Applications of Modern Imaging Technology*, vol. 1894, The International Society of Optical Engineering, pp. 312–322, Jan. 17–19, 1993.

Bucholz, P.D., et al., "Halo Vest Versus Spinal Fusion for cervical injury: evidence from an outcome study," *J. Neurosurg.*, vol. 70, No. 6, pp. 884–892, Jun. 1989.

Bucholz, R.D., et al., "Use of an Intraoperative Optical Digitizer in a System for Free–Hand Stereotactic Surgery," Poster #1120, *Scientific Program*, 1992 Annual Meeting, American Association of Neurological Surgeons, San Francisco, CA, Apr. 11–16, 1992, pp. 284–285.

Bucholz, R.D., et al., "Variables Affecting the Accuracy of Stereotactic Localization Using Computerized Tomography," *J. Neurosurg.*, vol. 79, pp. 667–673, Nov. 1993.

Bullard, D.E., et al., "CT–Guided Stereotactic Biopsies Using a Modified Frame and Gildenberg Techniques" (Jan. 5, 1984).

BYTE Magazine, "3–D Digitizer Captures the World" (Oct. 1990), p. 43.

Champleboux, "Utilisation De Fonctions Splines Pour La Mise Au Point d'Un Capteur Tridimensional Sans Contact," (Jul. 1991).

Champleboux, et al., "Accurate Calibration of Cameras and Range Imaging Sensors: the NPBS Method," 6 pages (1992).

Cinquin, et al., "Computer Assisted Medical Inverventions," The $1^{st}$ Workshop on Domestic Robotics—The $2^{nd}$ Workshop on Medical & Healthcare Robotics, Sep. 5–7, 1989, pp. 65–5.

Cinquin, et al., "IGOR: Image Guided Operating Robot, Methodology, Applications," *IEEE EMBS*, Paris, pp. 1–2 (1992).

Clarysse, Patrick, et al., "A Computer–Assisted System for 3–D Frameless Localization in Stereotaxic MRI," *IEEE TOMA*, vol. 10, No. 4, pp. 523–529, Dec. 1991.

Dever, B. and Zinreich, M.D., S.J., "OR role seen for 3–D imaging," *Radiology Today*, 2 pages, Feb. 1991.

Foley, K.T., et al., "Image–Guided Intraoperative Spinal Localization," *Intraoperative Neuroprotection*, Chapter 19, pp. 325–340, 1996.

Friets et al., "A Frameless Stereotaxic Operating Microscope for Neurosurgery," *IEEE Transactions on Biomedical Engineering* 36, No. 6 (Jun. 1989), pp. 608, 613–617.

Gallen, C.C., et al., "Intracranial Neurosurgery Guided by Functional Imaging," *Surg. Neurol.*, vol. 42, pp. 523–530, Jan. 3, 1994.

Galloway, R.L., Jr. et al., "Interactive Image–Guided Neurosurgery," *IEEE TOMA*, vol. 39, No. 12, pp. 1228–1231, Dec. 1992.

Gildenberg, Philip L., M.D., et al., "Calculation of Stereotactic Coordinates from the Computed Tomographic Scan," *Neurosurgery*, vol. 10, No. 5, 1982, pp. 580–586.

Glaser, E.M., et al., "The Image–Combining Computer Microscope–an Interactice Instrument for Morphometry of the Nerous System," *Journal of Neuroscience Methods*, vol. 8, pp. 17–32, 1983.

Gleason, Curtis A., Ph.D., et al., "Stereotactic Localization (with Computerized Tomographic Scanning), Biopsy, and Radiofrequency Treatment of Deep Brain Lesions," *Neurosurgery*, vol. 2, No. 3, 1978, pp. 217–222.

Golfinos, J.G., et al., "Clinical Use of a Frameless Stereotaxic Arm: results of 325 cases," *J. Neurosurg.*, vol. 83, No. 3, pp. 197–205, Aug. 1995.

Gomez, C.R., et al., "Transcranial Doppler Ultrasound Following Closed Head Injury: Vasospasm or Vasoparalysis?," *Surg. Neurol*, vol. 35, No. 1, pp. 30–35, Jan. 1991.

Gouda, Kasim I., M.D., et al., "New frame for stereotaxic surgery," *J. Neurosurg.*, vol. 53, 1980, pp. 256–259.

Greitz, T., et al., "Head Fixation System for Integration of Radiodiagnostic and Therapeutic Procedures," *Neuroradiology*, vol. 19, No. 1, 1980, pp. 1–6.

Hahn, Joseph F., N.D., et al., "Needle Biopsy of Intracranial Lesions Guided by Computerized Tomography," *Neurosurgery*, vol. 5, No. 1., 1979, pp. 11–15.

Hanson, Gayle, "Robots Roll into Operating Rooms," *Insight*, Apr. 8, 1991, pp. 44–45.

Hatch, J.F., et al., "Reference–Display System for the Integration of CT Scanning and the Operating Microscope," Proceedings of the Eleventh Annual Northeast Bioengineering Conference, Mar. 14–15, 1985, *IEEE* 1985, pp. 252–254; Trustees of Dartmouth College, Oct. 1984, entire thesis.

Heilbrun, M.P., "Computer Tomography–Guided Stereotactic Systems" (1983).

Heilburn, M. Peter, et al., "Preliminary Experience with a Brown–Roberts–Wells (BRW) Computerized Tomography Stereotaxic Guidance System," *J. Neurosurg.*, vol. 59, pp. 217–222, Aug. 1983.

Henderson, J.M., et al., "An Accurate and Ergonomic Method of Registration for Image–Guided Neurosurgery," Computerized Medical Imaging and Graphics, vol. 18, 4, pp. 273–277, 1994.

Hinck, Vincent C., M.D., et al., "A precise technique for craniotomy localization using computerized tomography," *J. Neurosurg*, vol. 54, Mar. 1981, pp. 416–418.

Hoerenz, Peter, "The Operating Microscope, I., Optical Principles, Illumination Systems, and Support Systems," *Journal of Microsurgery*, vol. 1, Mar.–Apr. 1980, pp. 364–369.

Holman, B. Leonard, et al., "Computer–Assisted Superimposition of Magnetic Resonance and High–Resolution Technetium–99–m–HMPAO and Thallium–201 SPECT Images of the Brain," *The Journal of Nuclear Medicine*, vol. 32, No. 8, Aug. 1991, pp. 1478–1484.

Horner, N.B., et al., "A Comparison of CT–Stereotaxic Brain Biposy Techniques" (Apr. 12, 1984).

Hounsfield, G.N., "Computerized transverse axial scanning (tomography): Part 1., Description of System," *British Journal of Radiology*, vol. 46, 1973, pp. 1016–1022.

Jacques, et al., "A Computerized Microstereotactic Method to Approach, 3–Dimensionally Reconstruct, Remove and Adjuvantly Treat Small CNS Lesions," *Appl. Neurophysiol.*, vol. 43, pp. 176–182 (1980).

Jacques, Skip, M.D., et al., "Computerized three–dimensional stereotaxic removal of small central nervous system lesions in patients," *J. Neurosurg*, vol. 53, Dec. 1980, pp. 816–820.

Kato et al., "A Frameless, Armless Navigational System for Computer Assisted Neurosurgery", 74 *J. Neurosurg.*, 845–849, 1991.

Kaufman, Howard H., M.S., "New Head–positioning System for Use with Computed Tomographic Scanning," *Neurosurgery*, vol. 7, No. 2, 1980, pp. 147–149.

Kelly, P.J., et al., "Computer–Assisted Stereotaxic Laser Resection of Intra–Axial Brain Neoplasma" (Mar. 1986).

Kelly, P.J., et al., "Precision Resection of Intra–Axial CNS Lesions by CT–Based Stereotactic Craniotomy and Computer Monitored CO2 Laser," *Acta Neurochirurgica*, 1983, 68, pp. 1–9.

Kelly, Patrick, J., et al., "A Microstereotactic Approach to Deep–seated Arteriovenous Malformations," *Surgical Neurology*, vol. 17, No. 4, Apr. 1982, pp. 260–262.

Kelly, Patrick J., et al., "A Stereotactic Approach to Deep–Seated Central Nervous System Neoplasms Using the Carbon Dioxide Laser," *Surgical Neurology*, vol. 15, No. 5, May 1981, pp. 331–334.

Kelly, Patrick J., et al., "Stereotactic CT Scanning for the Biopsy of Intracranial Lesions and Functional Neurosurgery," *Applied Neurophysiology*, Dec. 1983, Karger, AG, pp. 193–199.

Kosugi, Y., et al., "An Articulated Neurosurgical Navigation System Using MRI and CT Images" (Feb. 1988).

Laitinen, L.V., "Trigeminus Stereoguide: An Instrument for Stereotactic Approach Through the Foramen Ovale and Foramen Jugulare" (1984).

Lavallee, S., et al., "Matching 3–D Smooth Surfaces with their 2–d Projections using 3–D Distance Maps," *SPIE*, vol. 1570, 1991, pp. 322–336.

Lavallee, et al., "Computer Assisted Puncture," pp. 439–449 (Nov. 16–20, 1987).

Lavallee, et al., "Computer Assisted Medical Interventions," NATA ASI, vol.F60, pp. 301–312 (1990).

Lavallee, et al., "Computer Assisted Interventionist Imaging: The Instance of Stereotaactic Brain Surgery," *Medinfo Magazine*, pp. 613–617 (1989).

Lavallee, "A New System for Computer Assisted Neurosurgery," *IEEE*, (1989).

Lavallee, et al., "Matching of Medical Images for Computed and Robot Assisted Surgery," 2 pages (Nov. 1989).

Leksell, L., et al., "Stereotaxis and Tomography, A Technical Note," *Acta Neurochirurgica*, vol. 52, Fasc–12, 1980, pp. 1–7.

Lemke, et al., "Computer Assisted Driving of a Needle into the Brain," *Computer Assisted Radiology Magazine*, pp. 416–420 (1989).

Levin, David N., et al., "The Brain: Integrated Three–Dimensional Display of MR and PET Images," *Radiology*, Sep. 1989, vol. 172, No. 3, pp. 783–789.

Levin, D., et al., "Multimodality 3–D View of the Brain Created from MRI and PET Scans," *SMRI 1989: Seventh Annual Meeting Program and Abstracts*, vol. 7, Supplement 1, p. 89.

Levinthal, Robert, M.D., et al., "Technique for Accurate Localization with the CT Scanner," *Bulletin of the Los Angeles Neurological Societies*, vol. 41, No. 1, Jan. 1976, pp. 6–8.

Lunsford, L. Dade, M.D., "Innovations in Stereotactic Technique Coupled with Computerized Tomography," *Contemporary Neurosurgery*, 1982, pp. 1–6.

MacKay, Alexander R., M.D., et al., "Computed Tomography–directed Stereotaxy for Biopsy and Interstitial tradition of Brain Tumors: Technical Note," *Neurosurgery*, vol. 11, No. 1, Jul. 1982, pp. 38–42.

Maroon, Joseph C., M.D., et al., "Intracranial biopsy assisted by computerized tomography," *J. Neurosurg.*, vol. 46, No. 6, Jun. 1977, pp. 740–744.

Mazier, et al., "Computer Assisted Interventionist Imaging: Application to the Vertebral Column Surgery," *IEEE*, vol. 12, No. 1 (1990).

Mazier, et al., "Computer Assisted Vertebral Column Surgery: Application to the Spinal Pedicle Fixation," *Innov. Tech. Biol. Med.*, vol. 11/5 (1990), pp. 559–566.

Mazier et al., "Chirurgie De La Colonne Vertebrate Assiste Par Ordinateur: Application Au Vissage Pediculaire," *Innov. Tech. Biol. Med.*, vol. 11, No. 5, pp. 559–566, 1990.

Mesqui, F., et al., "Real–Time Noninvasive Recording and Three–Dimensional Display of the Functional Movements of an Arbitrary Mandible Point," *SPIE Biostereometrics '85*, vol. 602, pp. 77–84, Dec. 3–6, 1985.

Moran, Christopher J., M.D., et al., "Central Nervous System Lesions Biopsied or Treated by CT–guided Needle Placement," *Radiology*, vol. 131, No. 3, Jun. 1979, pp. 681–686.

Mosges, R., et al., "A New Imaging Method for Intraoperative Therapy Control in Skull–Base Surgery" (1988).

Mundinger, F., et al., "Treatment of Small Cerebral Gliomas with CT–Aided Stereotaxic Curietherapy," *Neuroradiology*, vol. 16, Jun. 4–10, 1978, pp. 564–567.

Mundinger, F., et al., "Computer–Assisted Stereotactic Brain Operations by Means Including Computerized Axial Tomography," *Applied Neurophysiology*, vol. 41, No. 1–4, 1978, pp. 169–182.

Norman, David, M.D., et al., "Localization with the EMI Scanner," *The American Journal of Roentgenology, Radium Therapy and Nuclear Medicine*, vol. 125, No. 4, Dec. 1975, pp. 961–964.

O'Leary, Daniel H., M.D., et al., "Localization of vertex lesions seen on CT scan," *J. Neurosurg*, vol. 49, No. 1, Jul. 1978, pp. 71–74.

Olivier, A., et al., "Frameless stereotaxy for surgery of the epilepsies: preliminary experience" *J. Neurosurg.*, vol. 81, No. 4, pp. 628–633, Oct. 1994.

Patil, A–A., "Computed Tomography Plane of the Target Approach in Computed Tomographic Stereotaxis"(1984).

Paul, et al., "Development of a Surgical Robot for Cementless Total Hop Arthroplasty," *Clinical Orthopaedics*, Apr. 21, 1992, pp. 58–60.

Pelizzari, C.A., et al., "3D Patient/Image Registration: Application to Radiation Treatment Planning," *Medical Physics*, vol. 18, No. 3, May/Jun. 1991, p. 612.

Pelizzari, C.A., et al., "Three Dimensional Correlation of PET, CT and MRI Images," *The Journal of Nuclear medicine, Abstract Book*, 34th Annual Meeting, Toronto, Canada, 1987, vol. 28, No. 4, Poster Session No. 528, p. 682.

Pelizzari, C.A., et al., "Accurate Three–Dimensional Registration of CT, PET and/or MR Images of the Brain," *Journal of Computer Assisted Tomography*, 13(1):20–26, Jan./Feb. 1989, Raven Press, pp. 20–26.

Pelizzari, C.A., et al., "Interactive 3D Patient–Image Registration," *Lecture Notes in Computer Science*, Springer–Verlag, Wye, UK, 1991 Proceedings, pp. 132–141.

Pelizzari et al., "Interactive 3D Patient–Image Registration" *Information Processing in Medical Imaging, Proceedings*, (Jul., 1991), pp. 132–141.

Pelizzari, C.A., et al., "Interactive 3D Patient–Image Registration" *Information Procession in Medical Imaging, Proceedings*, pp. 132–141, Jul. 1991.

Penn, R.D., et al., "Stereotactic Surgery with Image Processing of Computerized Tomographics Scans," *Neurosurgery*, vol. 3, No. 2, pp. 157–163, May 26, 1978.

Perry, John H., Ph.D., et al., "Computed Tomography–guided Stereotactic Surgery: Conception and Development of a new Stereotactic Methodology," *Neurosurgery*, vol. 7, No. 4, Oct. 1980, pp. 376–381.

Picard, C., et al., "The First Human Stereotaxic Apparatus" *J. Neurosurg.*, vol. 59, pp. 673–676, Oct. 1983.

Piskun, Walter, S., Major, et al., "A Simplified Method of CT Assisted Localization and Biopsy of Intracranial Lesions," *Surgical Neurology*, vol. II,, Jan.–Jun. 1979, pp. 413–417.

Pixsys, Inc., "PixSys 3–D digitizing Accessories" (Aug. 1989), 6 unnumbered pages.

Pixsys, Inc., "Offset Probe for Science Accessories' GP–8–3d digitizer" (Dec. 1987), one page.

Pixsys, Inc., "SACDAC User's Guide, Version 2e" (Mar. 1980) pp. 0–1 through 5–3.

Pixys, Inc., "Design Aide" (Mar. 1989) 5 unnumbered pages.

Reinhardt et al., "CT–Guided 'Real Time' Stereotaxy," *Acta Neurochirurgica Suppl. 46*, pp. 107–108 (1989).

Reinhardt et al., "A Computer Assisted Device for the Intraoperate Ct–Correlated Localization of Brain Tumors," (1988) Eur. Surg. Res. 20:52–58.

Reinhardt, "Surgery of Brain Neoplasms Using 32–P Tumour Marker," *Acta Neurochir.* 97, pp. 89–94, (1989).

Reinhardt et al., "Sonic Stereometry in Microsurgical Procedures for Deep–Seated Brain Tumors and Vascular Malformations," *Neurosurgery*, vol. 32, No. 1, (Jan. 1993).

Reinhardt et al., "Interative Sonar–Operated Device for Stereotactic and Open Surgery," *Stereotac Funct Neurosurg*, 1990, pp. 54, 55, 393–397.

Reinhardt et al., "Mikrochirurgische Entfernung tiefliegender Gefaβbildungen mit Hilfe der Sonar–Stereometrie," *Ultra–schall in Med.*, vol. 12, pp. 80–84, (1991).

Roberts, D.W., et al., "A Frameless Stereotaxic Integration of Computerized Tomographic Imaging and the Operating Microscope" (Oct. 1986).

Roberts et al., "A Frameless Stereotaxic Integration of Computerized Tomography Imaging and the Operating Microscope" *J. Neurosurg*, 65:545–549 (1986), pp. 545–549.

Rosenbaum, Arthur E., et al., "Computerized Tomography Guided Stereotaxis: A New Approach," *Applied Neurophysiology*, vol. 43, Nos. 3–5, Jun. 4–7, 1980, pp. 172–173.

Sautot, et al., "Computer Assisted Spine Surgery: a First Step Toward Clinical Application in Orthopaedics," *IEEE*, (1992).

Scarabin, J.M., et al., "Stereotaxic Exploration in 200 Supratentorial Brain Tumors," *Neuroradiology*, vol. 16, Jun. 4–10, 1978, pp. 591–593.

Shelden, C.H., et al., "Development of a computerized microstereotaxic method for localization and removal of minute CNS lesions under direct 3–D vision," *J. Neurosurg.*, vol. 52, Jan. 1980, pp. 21–27.

Simon et al., "The Neurostation TM10A Highly Accurate, Minimally Invasive Solution to Frameless Stereotactic Neurosurgery," *Computerized Medical Imaging and Graphics*, vol. 18, No. 4, pp. 247–256, 1994.

Shiu, Y.C., "Finding the Mounting Position of a Sensor by Solving a Homogenous Transform Equation of Form AX=XB," *IEEE*, 1987,pp. 1666–1671.

Smith, Kurt R., et al., "Multimodality Image Analysis and Display Methods for Improved Tumor Localization in Stereotactic Neurosurgery," *Annual Conference of the IEEE Engineering in Medicine and Biology Society*, vol. 13, No. 1, pp. 0210, 1991.

Smith, Kurt R., et al., "Computer Methods for Improved Diagnostic Image Display Applied to Stereotactic Neurosurgery," *Automedica*, vol. 14, pp. 371–382, 1992.

Smith, Kurt R., et al., "The Neurostation TM10A Highly Accurate, Minimally Invasive Solution to Frameless Stereotactic Neurosurgery," *Computerized Medical Imaging and Graphics*, vol. 18, No. 4, pp. 247–256, 1994.

Spencer, et al., "Unilateral Transplantation of Human Fetal Mesencephalic Tissue into the Caudate Nucleus of Patients with Parkinson's Disease" *The New England Journal of Medicine*, vol. 327, No. 22, pp. 1541–1548, Nov. 26, 1992.

Valentino, D.J., et al., "Three–Dimensional Visualization of Human Brain Structure–Function Relationships," *The Journal of Nuclear Medicine*, Oct. 1989, Posterboard 1136, vol. 30, No. 10, p. 1747.

Van Buren, J.M., et al., "A Multipurpose CT–Guided Stereotactic Instrument of Simple Design" (1983).

Watanabe et al., "Three Dimensional Digitizer (Neuronavigator) New Equipment for Computed Tomography–Guide Stereotaxic Surgery" (1987), 27 Surg. Neurol., 543–7.

Watanabe, "Neuronavigator," *Igaku–no–Ayumi*, vol. 137, No. 6 (May 10, 1986).

Yeates, Andrew, M.D., et al., "Simplified and accurate CT–guided needle biopsy of central nervous system lesions," *Journal of Neurosurgery*, vol. 57, No. 3, pp. 390–393, (Sep. 1982).

Yosugi et al., "An Articulated Neurosurgical Navigation System Using MRI and CT Images," (Feb. 1988) pp. 147–152.

\* cited by examiner

FIG. 1
PRIOR ART
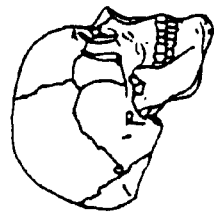
POSITION IN SURGERY
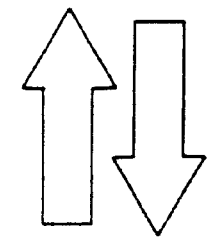
REGISTRATION
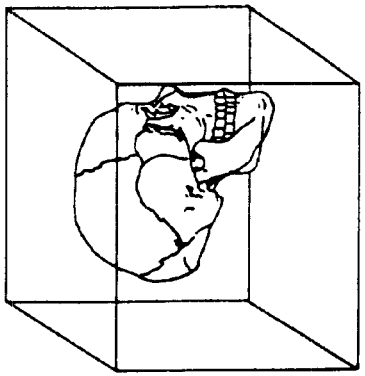
PRE-SURGICAL SCANS (IMAGE DATASET)

SYSTEM FOR USE IN DISPLAYING IMAGES OF A BODY PART

This application is a continuation of Ser. No. 08/931,654, filed Sep. 16, 1997, (now U.S. Pat. No. 6,347,240) which is a continuation of Ser. No. 08/319,615, filed Oct. 7, 1994 (abandoned), which is a continuation-in-part of Ser. No. 08/053,076 filed Apr. 26, 1993 (abandoned), which is a continuation-in-part of Ser. No. 07/909,097, filed Jul. 2, 1992 (now U.S. Pat. No. 5,383,454) which is a continuation of Ser. No. 07/600,753, filed Oct. 19, 1990 (abandoned), all of which are incorporated herein by reference.

BACKGROUND OF THE INVENTION

The invention relates generally to systems which generate images during medical and surgical procedures, and in particular, a system for generating images during medical and surgical procedures based on a scan taken prior to the procedure.

Image guided medical and surgical procedures comprise a technology by which images, obtained either pre-procedurally or intra-procedurally (i.e., prior to or during a medical or surgical procedure), are used to guide a doctor during the procedure. The recent increase in interest in this field is a direct result of the recent advances in imaging technology, especially in devices using computers to generate three dimensional images of parts of the body, such as computed tomography (CT) or magnetic resonance imaging (MRI).

The majority of the advances in imaging involve devices which tend to be large, encircle the body part being imaged, and are expensive. Although the images produced by these devices depict the body part under investigation with high resolution and good spatial fidelity, their cost usually precludes the dedication of a unit to the performance of procedures. Therefore, image guided surgery is usually performed using images taken preoperatively.

The reliance upon preoperative images has focused image guidance largely to the cranium. The skull, by encasing the brain, serves as a vessel which inhibits changes in anatomy between imaging and surgery. The skull also provides a relatively easy point of reference to which a localization system may be attached so that registration of pre-procedural images to the procedural work space can be done simply at the beginning of the procedure. Registration is defined as the process of relating pre-procedural images of anatomy to the surgical or medical position of the corresponding anatomy. For example, see Ser. No. 07/909,097, now U.S. Pat. No. 5,383,454, the entire disclosure of which is incorporated herein by reference.

This situation of rigid fixation and absence of anatomical movement between imaging and surgery is unique to the skull and intracranial contents and permits a one-to-one registration process as shown in FIG. 1. The position during a medical procedure or surgery is in registration with the pre-procedural image data set because of the absence of anatomical movement from the time of the scan until the time of the procedure. In almost every other part of the body there is ample opportunity for movement which degrades the fidelity of the pre-procedural images in depicting the intra-procedural anatomy. Therefore, additional innovations are needed to bring image guidance to the rest of the body beyond the cranium.

The accuracy of image guided surgery is based on the identification of structures within the body that do not change shape, do not compress, nor deform between the process of imaging and surgery. Such structures are termed "rigid bodies," and the bones of the skeleton satisfy this definition for a rigid body. Bones are commonly a target for medical or surgical procedures either for repair, fusion, or biopsy. Therefore, a technique is needed whereby registration can be performed between the bones or bone fragments (skeletal elements) as depicted pre-procedurally on scans and the position of these same skeletal elements as detected intra-procedurally. This technique must take into account that movement can occur between portions of the skeleton which are not rigidly joined, such as bones connected by a joint, or fragments of a broken bone.

SUMMARY OF THE INVENTION

It is an object of this invention to provide a system which allows registration between multiple skeletal elements depicted in pre-procedural images and detected during surgery.

It is a further object of this invention to provide a system which can localize multiple rigid bodies that move with respect to each other between imaging and a procedure and provide a display during the procedure of the bodies in their displaced positions.

It is another object of this invention to provide a system for use during a medical or surgical procedure on the body, the system generating a display representing the position of two or more body elements during the procedure based on an image data set generated by a scanner prior to the procedure.

It is another object of this invention to provide a system for use during a medical or surgical procedure on a body which modifies the image data set according to the identified relative position of each of the elements during the procedure.

It is another object of this invention to provide a system which generates a display representative of the position of a medical or surgical instrument during a procedure in relation to body elements.

It is a further object of this invention to provide a system for use during image guided medical and surgical procedures which is easily employed by the doctor or surgeon conducting the procedure.

It is another object of this invention to provide a system which determines the relative position of body elements based on the contour of the body elements which, in some cases, avoids the need for exposing the body elements.

It is still another object of this invention to provide a system which employs the projected fluoroscopic images of body elements to determine their relative position.

It is yet a further object of this invention to describe a surgical or medical procedure which employs a display representing the position of body elements during the procedure based on an image data set of the body elements generated prior to the procedure.

It is a further object of this invention to provide a system and method for medical or surgical procedures which allows repositioning of body elements during the procedure and still permits the generation of a display showing the relative position of the body elements.

Other objects and features will be in part apparent and in part pointed out hereinafter.

The invention comprises a system for use during a medical or surgical procedure on a body. The system generates a display representing the position of two or more body elements during the procedure based on an image data set generated by a scanner prior to the procedure, the image data set having reference points for each of the body elements. The reference points of a particular body element have a fixed spatial relation to the particular body element. The system includes means for identifying, during the procedure, the relative position of each of the reference points of each of the body elements to be displayed. The system also includes a processor modifying the image data set according to the identified relative position of each of the reference points during the procedure, as identified by the identifying means. The processor generates a displaced image data set representing the position of the body elements during the procedure. The system also includes a display utilizing the displaced image data set generated by the processor and illustrating the relative position of the body elements during the procedure.

The invention also comprises a method for use during a procedure. The method generates a display representing the position of two or more body elements during the procedure based on an image data set generated prior to the procedure, which image data set has reference points for each of the body elements. The method comprises the steps of:

identifying, during the procedure, the relative position of each of the reference points of each of the body elements to be displayed;

modifying the image data set according to the identified relative position of each of the reference points during the procedure in order to generate a displaced image data set representing the position of the body elements during the procedure; and generating a display based on the displaced image data set illustrating the relative position of the body elements during the procedure.

The invention also comprises a method for use with two or more body elements which each have reference points. The method comprises the steps of:

prior to a procedure:

placing the body elements in a frame to fix their relative position; and scanning the fixed body elements; and during the procedure:

placing the body elements in the frame so that the body elements have the same relative position as their position during scanning;

determining the position of reference points on the body elements relative to reference means;

determining the position of a medical or surgical instrument relative to the reference means;

determining the position of the medical or surgical instrument relative to the body elements; and generating a display based on the pre-procedural scanning illustrating the determined position of the medical or surgical instrument relative to the body elements.

BRIEF DESCRIPTION OF THE DRAWINGS

FIG. 1 is an illustration of the prior art system in which rigid fixation and absence of movement between imaging and surgery permits a one-to-one registration process between the pre-surgical image data set and the position in surgery.

Corresponding reference characters indicate corresponding parts throughout the drawings.

DETAILED DESCRIPTION OF THE PREFERRED EMBODIMENTS

Figure 2A:
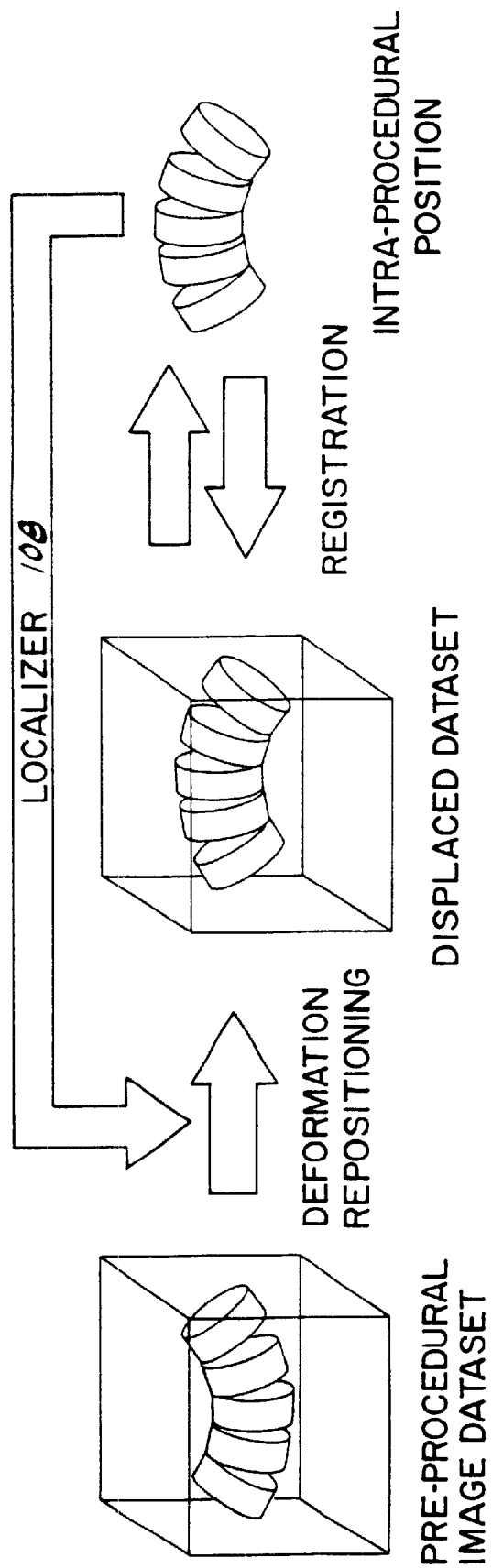
FIG. 2A is an illustration of operation of the invention in which the pre-procedural image date set is modified in accordance with the intra-procedural position in order to generate a displace data set representative of the intra-procedural position.
Figure 3:
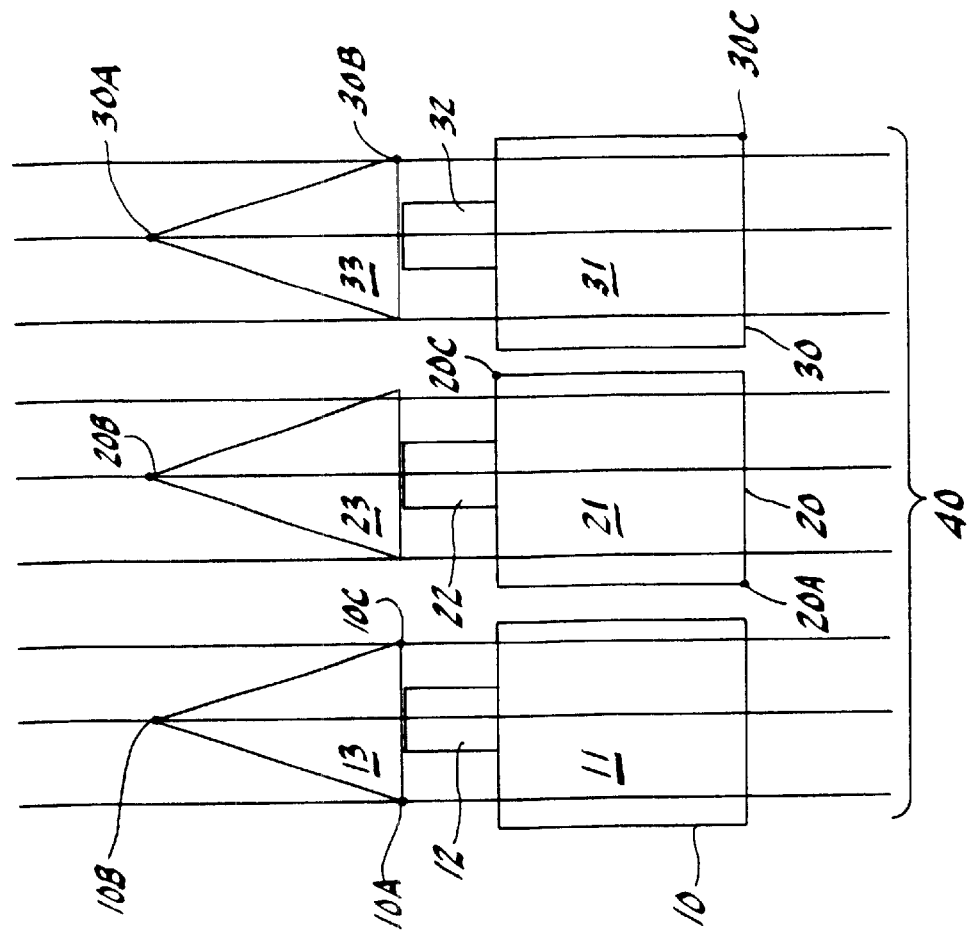
FIG. 3 is an illustration of the pre-procedural alignment of three body elements during scanning.

Referring to FIG. 2A, an overview of operation of one preferred embodiment of the system according to the invention is illustrated. Prior to a particular procedure, the body elements which will be part of the procedure are scanned to determine their alignment. For example, the alignment may be such as illustrated in FIG. 3 wherein body elements 10, 20, and 30 are more or less aligned in parallel. These body elements may be bones or other rigid bodies. In FIG. 3, three-dimensional skeletal elements 10, 20, 30 are depicted in two dimensions as highly stylized vertebral bodies, with square vertebra 11, 21, 31, small rectangular pedicles 12, 22, 32, and triangular spinous processes 13, 23, 33. During imaging, scans are taken at intervals through the body parts 10, 20, 30 as represented in FIG. 3 by nine straight lines generally referred to be reference character 40. At least one scan must be obtained through each of the body elements and the scans taken together constitute a three-dimensional pre-procedural image data set.

Figure 2B:
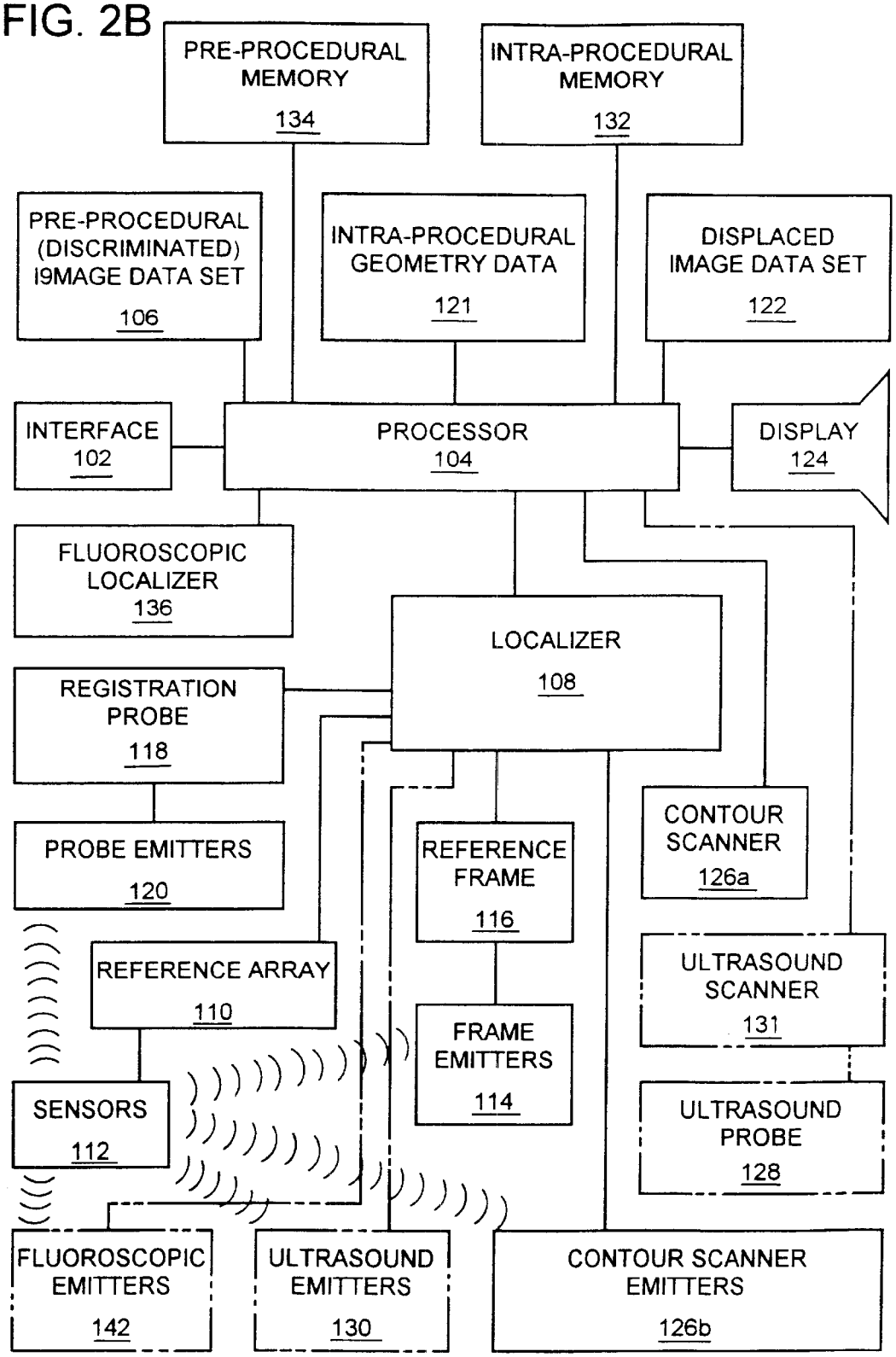
FIG. 2B is a block diagram of one preferred embodiment of a system according to the invention.

FIG. 2B is a block diagram of the system according to the invention. A scanner interface 102 allows a processor 104 to obtain the pre-procedural image data set generated by the scanner and store the data set in pre-procedural image data set memory 106. Preferably, after imaging, processor 104 applies a discrimination process to the pre-procedural image data set so that only the body elements 10, 20, 30 remain in memory 106. If a discrimination process is employed, processor 104 may execute the discrimination process while data is being transferred from the scanner through the scanner interface 102 for storage in memory 106. Alternatively, memory 106 may be used for storing undiscriminated data and a separate memory (not shown) may be provided for storing the discriminated data. In this alternative, processor 104 would transfer the data set from the scanner through scanner interface 102 into memory 106 and then would discriminate the data stored in memory 106 to generate a discriminated image data set which would be stored in the separate memory.

Once the body elements 10, 20, 30 are discriminated from the soft tissue and each defined as a single rigid body, they can be repositioned by software algorithms, well known in the art, to form the displaced image data set. Each of the body elements 10, 20, 30 must have at least three reference points which are selected by the doctor or surgeon and which are visible on the pre-procedural images. These reference points must be able to be indicated with accuracy during the procedure. For body part 10, reference points 10A, 10B, and 10C are located on the spinous process 13; for body part 20, reference points 20A and 20C are located on the vertebra 21 and reference point 20B is located on spinous process 23; and for body part 30, reference points 30A and 30B are located on the spinous process 33 and reference point 30C is located on the vertebra 31. More than one reference point can be selected on each scan through the bone, although the maximal accuracy of registration is achieved by separating the reference points as far as possible. For example, in the case of posterior spinal surgery, it may be preferable to select reference points 10A, 10B, and 10C on the spinous process which is routinely exposed during such surgery. It is contemplated that work station software may allow the manual or automated identification of these same points on the images of the body elements 10, 20, 30. As FIG. 3 is a two-dimensional simplification of a three-dimension process, the reference points will not necessarily be limited to a perfect sagittal plane, as depicted.

After imaging, the skeletal body elements 10, 20, 30 may move with respect to each other at the joints or fracture lines. In the procedure room, such as an operating room or a room where a medical procedure will be performed, after positioning the patient for surgery, the body elements will assume a different geometry, such as the geometry depicted in FIG. 4.

Figure 4:
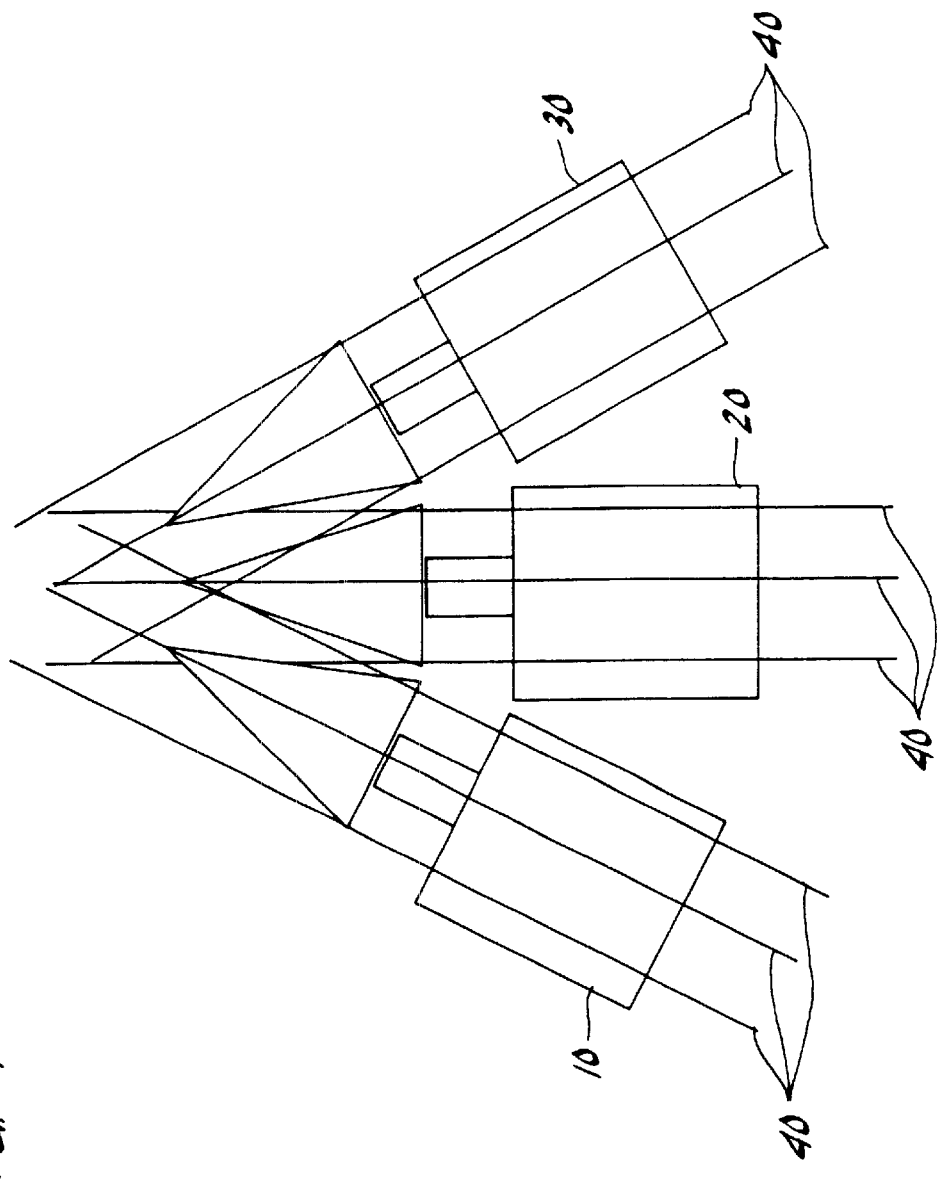
FIG. 4 is an illustration of the intra-procedural alignment of the three body elements of FIG. 3 during surgery.

As a result of this movement, the pre-procedural image data set stored in memory 106, consisting of the scans through the skeletal elements, does not depict the operative position of the skeletal elements, as shown in FIG. 4. However, the shape of the skeletal elements, as depicted by the scans through the element, is consistent between imaging and procedure, as indicated by the lines 40 through each element in FIG. 4. Therefore, the image data set must be modified to depict the current geometry of the skeletal elements. This modification is performed by identifying the location of each reference point of each skeletal element in procedure space. As diagrammatically illustrated in FIG. 2B, a localizer 108 identifies the location and provides this information so that the pre-procedural data set may be deformed or re-positioned into the displaced data set. As a result, the displaced data set is in registration with the intra-procedural position of the elements 10, 20, 30. Once the locations of the reference points are determined by the localizer 108, processor 104, which is a part of the work station, can execute software which re-positions the images of the skeletal elements to reflect the position of the actual elements in the procedure room thus forming the displace set and the registration between the displaced set and the intra-procedural position.

Preferably, a three-dimensional digitizer may be used as the localizer 108 to determine the position and space of the elements 10, 20, 30 during the procedure. In general, the digitizer would include a reference array 110 which receives emissions from a series of emitters. Usually, the emissions consist of some sort of energy, such as light, sound or electromagnetic radiation. The emitters are applied to and positioned in coordination with the elements being localized and the reference array 110 is distant therefrom, determining the position of the emitters. As is apparent, the emitters may be placed distant to the elements and the reference array 110 may be attached to the elements being localized.

Figure 5:
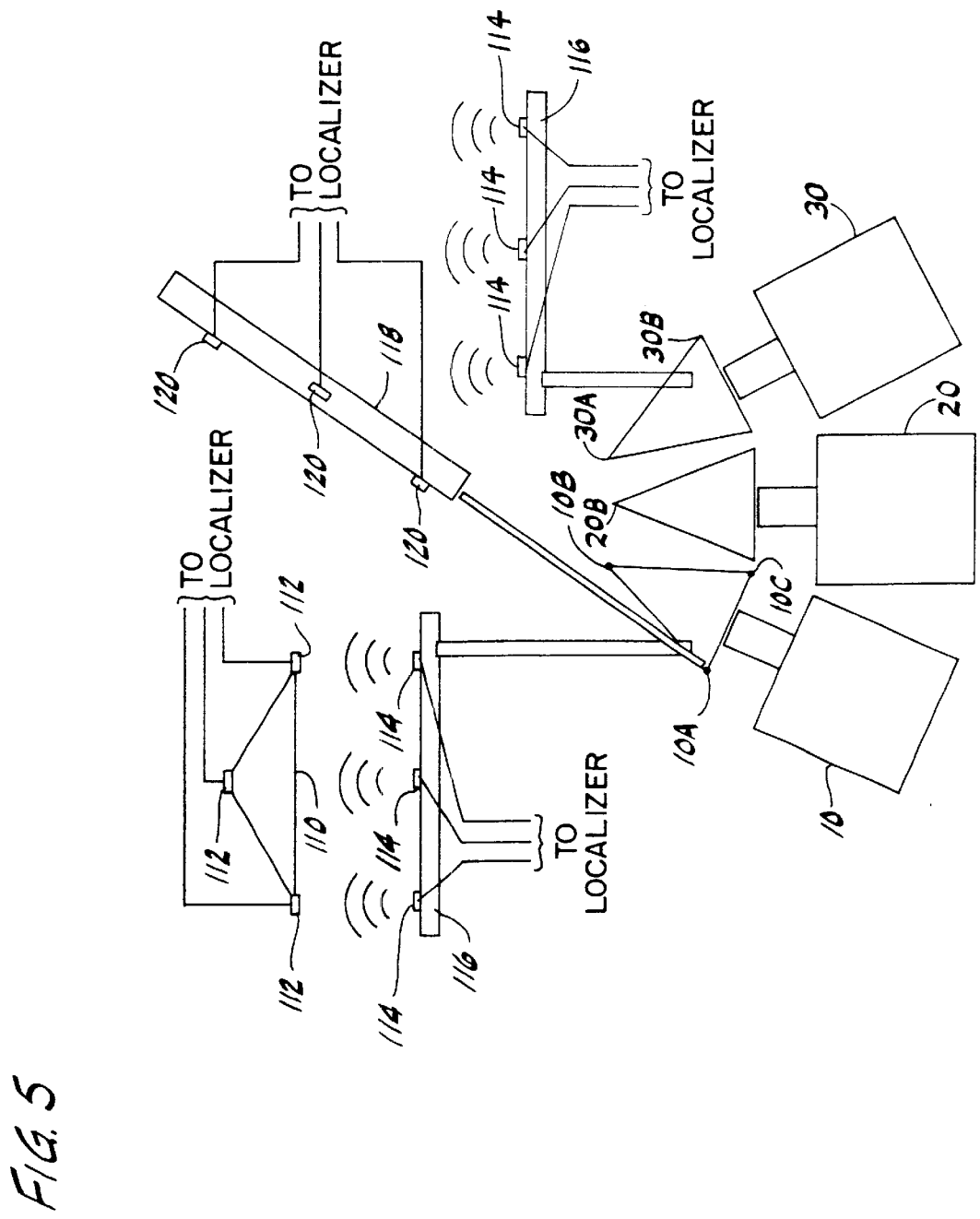
FIG. 5 is an illustration of three body elements, one of which has a reference frame attached thereto, in combination with a registration probe.

According to one preferred embodiment of the invention as shown in FIG. 5, a reference frame 116 is attached to one of the skeletal elements 10 at the beginning of the procedure. Reference frame 116 is equipped with a plurality of emitters 114 which together define a three-dimensional procedural coordinate system with respect to the skeletal element 10. Emitters 114 communicate with sensors 112 on a reference array 110 located in the procedure room and remote from the reference frame 116 and patient. If the body of the patient is not immobilized during surgery, then multiple reference frames may be required. The three-dimensional procedural coordinate system may alternatively be defined by rigid fixation of the frame emitters 114 directly (or indirectly, for example, to the skin) to the skeletal elements 10, 20, or 30. In either case, the emitters 114 emit a signal which is received by the sensors 112. The received signal is digitized to compute position, for example, by triangulation. Through such information, the localizer 108 or a digitizer which is part of the localizer 108 can determine the exact three-dimensional position of the frame emitters 114 relative to the sensors 112. The sensors 112 are in a fixed position throughout the procedure, as the reference array 110 is fixed in the procedure room to the ceiling or other support. Thereby, localizer 108 or the processor 104 can exactly determine the position of the reference frame 116 relative to the array. The reference frame 116 is free to move except during localization, e.g., activation of the emitters 114 on the reference frame 116 and activation of the probe emitters 120. Emitters 114 of the reference frame 116 are energized to provide radiation to the sensors 112, which radiation is received and generates signals provided to the localizer 108 for determining the position of the frame 116 relative to the array 110.

Next, it is necessary to determine the position of the skeletal element 10 to which the reference frame 116 is affixed. In particular, the position of the skeletal element 10 relative to the reference frame 116 must be determined. After exposure of the reference points 10A, 10B, 10C by surgical dissection, the reference points are touched by the tip of a registration probe 118 equipped with emitters 120. As each of the reference points 10A, 10B, 10C is touched by the tip of the probe 120, the emitters are energized to communicate with the sensors 112 of reference array 110. This communication permits the localizer 108 to determine the position of the registration probe 120, thereby determining the position of the tip of the probe 120, thereby determining the position of the reference point 10A on which the tip is positioned. By touching each of the reference points 10A, 10B, 10C on each skeletal element 10, 20, 30 involved in the procedure, and relating them to their corresponding reference points on the images of the same elements, an intra-procedural position data is generated and stored in memory 121. This data is used to derive a transformation which allows the determination of the exact procedural position and orientation of each skeletal element. Using the intra-procedural position of the skeletal elements 10, 20, 30, localizer 108 and processor 104 employ software which manipulates the pre-procedural image data set stored in memory 106 to produce a displaced image data set which is stored in memory 122. The displaced image data set in memory 122 reflects the geometry of the actual elements 10, 20, 30 during the procedure. Processor 104 displays the displaced image data set on display 124 to provide a visual depiction of the relative position of the skeletal elements 10, 20, 30 during the procedure. This image is used by the doctor during the procedure to assist in the procedure. In addition, it is contemplated that an instrument which would be used during the procedure may be modified by the addition of emitters. This modified instrument when moved into the area of the skeletal elements 10, 20, 30 would be activated so that its emitters would communicate with the reference array 110 thereby permitting localizer 108 to determine the instrument's position. As a result, processor 104 would modify display 124 to indicate the position of the instrument, such as by positioning a cursor.

Reference frame 116 allows the patient to be moved during the procedure without the need for re-registering the position of each of the body elements 10, 20, 30. It is assumed that during the procedure, the patient is immobilized so that the body elements are fixed relative to each other. Since the reference frame 116 is affixed to skeletal element 10, movement of the patient results in corresponding movement of the reference frame 116. Periodically, or after each movement of the patient, array emitters 114 may be energized to communicate with the sensors 112 of reference array 110 in order to permit localizer 108 to determine the position of the reference frame 116. Since the reference frame 116 is in a fixed position relative to element 10 and since we have assumed that elements 20 and 30 are in fixed relation to element 10, localizer 108 and/or processor 104 can determine the position of the elements. From this position, a displaced image data set memory can be created for display on display 124.

An alternative to touching the reference points A, B, C with the tip of the probe 118 would be to use a contour scanner 126. Such a device, using some form of energy such as sound or light which is emitted, reflected by the contour and sensed, would allow the extraction of a contour of the skeletal elements 10, 20, 30, thus serving as a multitude of reference points which would allow registration to occur. The registration process is analogous to the process described for ultrasound extracted contours below.

In certain situations, markers may be used on the skin surface as reference points to allow the transformation of the pre-procedural image data set into the displaced image data set. Reciprocally, skin surface fiducials applied at the time of imaging can be used to re-position the body to match the geometry during imaging and is described below.

Localization of skeletal elements 10, 20, 30 may be desired without intra-procedural exposure of the reference points A, B, C on those skeletal elements. Examples wherein the spine is minimally exposed include percutaneous biopsy of the spine or discectomy, spinal fixation, endoscopy, percutaneous spinal implant insertion, percutaneous fusion, and insertion of drug delivery systems. In this situation, localization of reference points on the skeletal elements must be determined by some form of imaging which can localize through overlying soft tissue. There are currently two imaging techniques which are available to a surgeon in the operating room or a doctor in a procedure room which satisfy the needs of being low cost and portable. Both imaging techniques, ultrasonography and radiography, can produce two- or three-dimensional images which can be employed in the fashion described herein to register a three-dimensional form such as a skeletal element.

Figure 6:
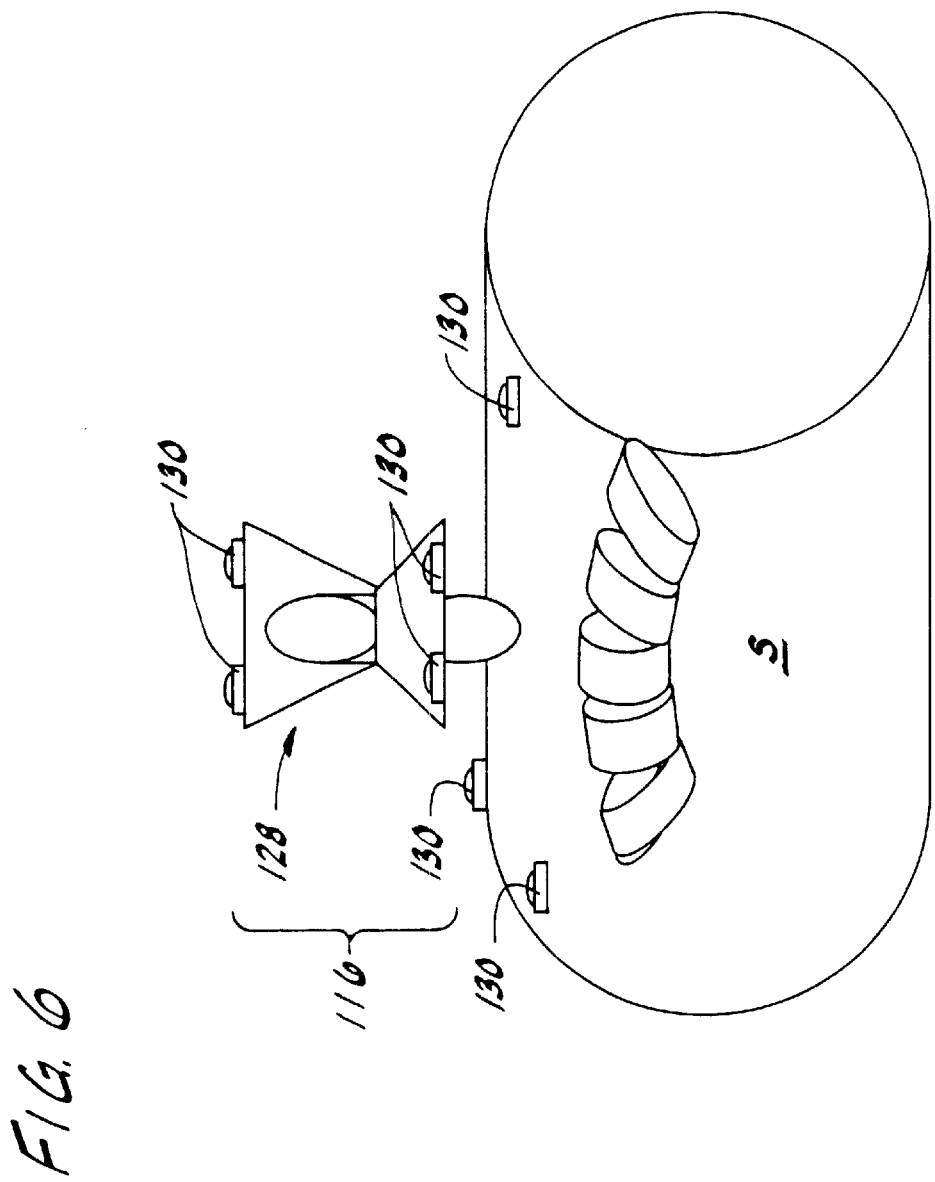
FIG. 6 is an illustration showing ultrasound registration according to the invention in which emitters are attached to the patient's body.

As described in U.S. patent application Ser. Nos. 07/858, 980 and 08/053,076, the entire disclosures of which are incorporated herein by reference, the coupling of a three-dimensional digitizer to a probe of an ultrasound device affords benefits in that a contour can be obtained which can be related directly to a reference system that defines three-dimensional coordinates in the procedural work space. In the context of the present invention, a patient is imaged prior to a procedure to generate a pre-procedural image data set which is stored in memory 106. In the procedure room, the patient's body is immobilized to stabilize the spatial relationship between the skeletal elements 10, 20, 30. A reference system for the body is established by attaching a reference array 110 to one of the skeletal elements or by otherwise attaching emitters to the patient or skeletal elements as noted above. For example, this could be performed by using the percutaneous placement of a reference system similar to the one described above, radiopaque markers screwed into the elements or by placing emitters 130 directly on the skins, as illustrated in FIG. 6, based on the assumption that the skin does not move appreciably during the procedure or in respect to the axial skeleton.

An ultrasound probe 128 equipped with at least three emitters 130 is then placed over the skeletal element of interest. The contour (which can be either two- or three-dimensional) of the underlying bone/soft tissue interface is then obtained using the ultrasound probe 128. This contour of the underlying bone can be expressed directly or indirectly in the procedural coordinates defined by the reference system. Emitters 130 communicate with sensors 112 of reference array 110 to indicate the position of the ultrasound probe 128. An ultrasound scanner 131 which energizes probe 128 determines the contour of the skeletal element of interest and being scanned. This contour information is provided to processor 104 for storage in contour memory 132.

The intra-procedural contour stored in memory 132 is then compared by a contour matching algorithm to a corresponding contour extracted from the pre-operative image data set stored in memory 106. Alternatively, a pre-procedural contour data set may be stored in memory 134 based on a pre-procedural ultrasound scan which is input into memory 134 via scanner interface 102 prior to the procedure. This comparison process continues until a match is found for each one of the elements. Through this contour matching process, a registration is obtained between the images of each skeletal element and the corresponding position of each element in the procedural space.

In certain instances, the ultrasound registration noted above may not be applicable. For example, ultrasound does not penetrate bone, and the presence of overlying bone would preclude the registration of an underlying skeletal element. Further, the resolution of ultrasound declines as the depth of the tissue being imaged increases and may not be useful when the skeletal element is so deep as to preclude obtaining an accurate ultrasonically generated contour. In these circumstances, a radiological method is indicated, which utilizes the greater penetrating power of x-rays.

Figure 7:
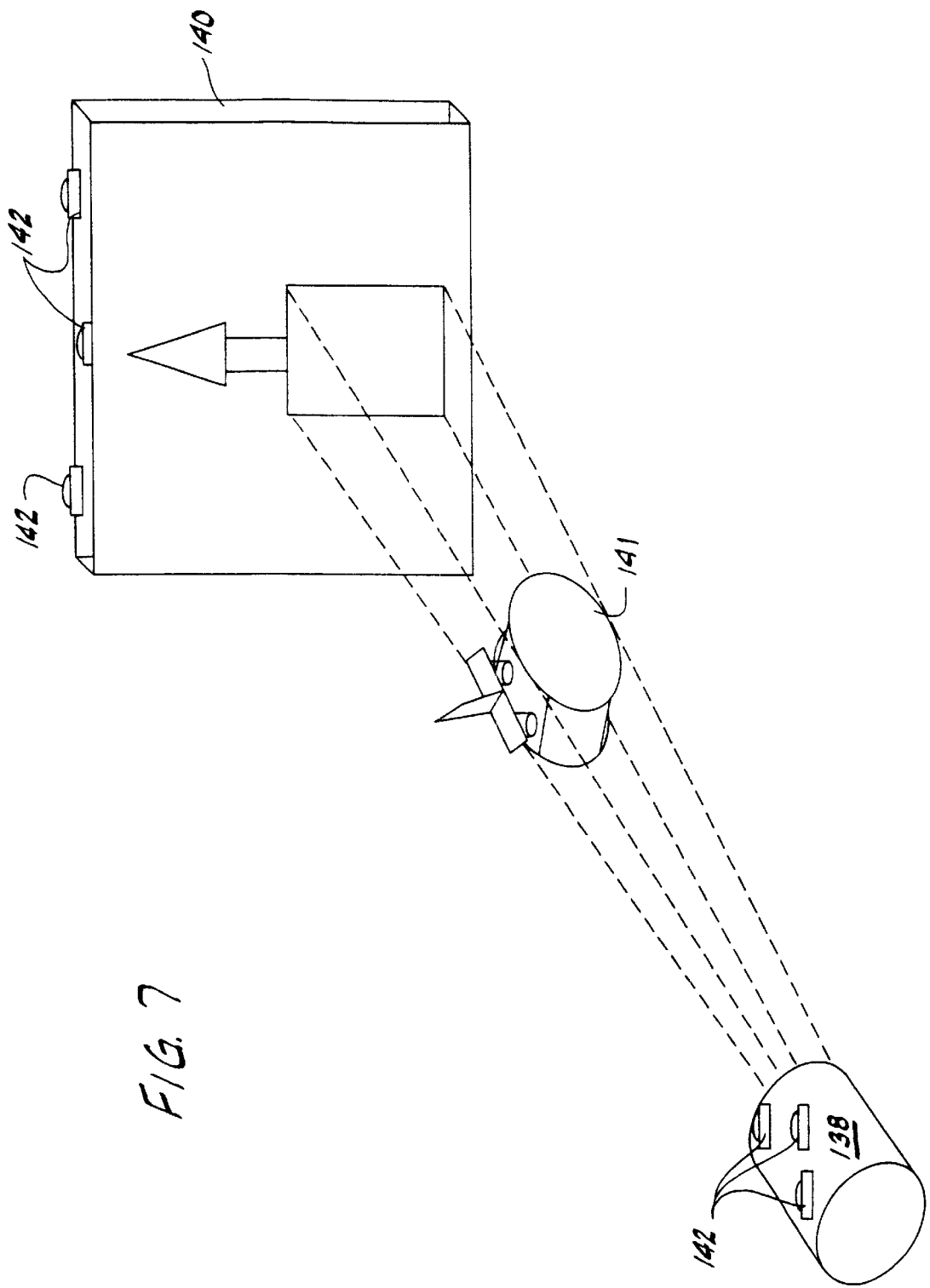
FIG. 7 is an illustration of a fluoroscopic localizer according to the invention for providing projections of an image of the body elements.

Pre-operative imaging occurs as usual and the skeletal elements are discriminated from the soft tissue in the image data set as above. In particular, a CT scan of the skeletal elements 10, 20, 30 is taken prior to the procedure. Processor 104 may then discriminate the skeletal elements. Next, the patient is immobilized for the procedure. A radiograph of the skeletal anatomy of interest is taken by a radiographic device equipped with emitters detectible by the digitizer. For example, a fluoroscopic localizer 136 is illustrated in FIG. 7. Localizer 136 includes a device which emits x-rays such as tube 138 and a screen 140 which is sensitive to x-rays, producing an image when x-rays pass through it. In general, this screen is referred to as a fluoroscopic plate. Emitters 142 may be positioned on the tube 138, or on the fluoroscopic plate 140 or on both. For devices in which the tube 138 is rigidly supported relative to the plate 140, emitters need only be provided on either the tube or the plate. Alternatively, the reference array 110 may be attached to the tube or the plate. By passing x-rays through the skeletal element 141 of interest, a two-dimensional image based on bone density is produced and recorded by the plate. The image produced by the fluoroscopic localizer 136 is determined by the angle of the tube 138 with respect to the plate 140 and the position of the skeletal elements therebetween. Fluoroscopic localizer 136 includes a processor which digitizes the image on the plate 140 and provides the digitized image to processor 104 for storage in memory 106. Processor 104 may simulate the generation of this two-dimensional x-ray image by creating a two-dimensional projection of the three-dimensional skeletal elements that have been discriminated in the image data set stored in memory 106. In order to form the displaced data set and thus achieve registration, an iterative process is used which re-positions the images of the skeletal elements such that a two-dimensional projection through the displaced data set matches the actual radiographic image. The described process can utilize more than one radiographic image. Since the processor 104 is also aware of the position of the fluoroscopic localizers because of the emitters 142 thereon, which are in communication with localizer 108, the exact position of the skeletal elements during the procedure is determined.

The above solutions achieve registration by the formation of a displaced image data set stored in memory 122 which matches the displacement of the skeletal elements at the time of the procedure. An alternative technique to achieve registration is to ensure that the positions of the skeletal elements during the procedure are identical to that found at the time of imaging. This can be achieved by using a frame that adjusts and immobilizes the patient's position. In this technique, at least three markers are placed on the skin prior to imaging. These markers have to be detectible by the imaging technique employed and are called fiducials. A multiplicity of fiducials is desirable for improving accuracy.

During the procedure, the patient's body is placed on a frame that allows precise positioning. Such frames are commonly used for spinal surgery and could be modified to allow their use during imaging and could be used for repositioning the patient during the procedure. These frames could be equipped with drive mechanisms that allow the body to be moved slowly through a variety of positions. The fiducials placed at the time of imaging are replaced by emitters. By activating the drive mechanism on the frame, the exact position of the emitters can be determined during the procedure and compared to the position of the fiducials on the pre-procedural image data set stored in memory 106. Once the emitters assume a geometry identical to the geometry of the fiducials of the image data set, it is considered that the skeletal elements will have resumed a geometric relationship identical to the position during the pre-procedural scan, and the procedure can be performed using the unaltered image data set stored in memory 106.

In general, instrumentation employed during procedures on the skeleton is somewhat different than that used for cranial applications. Rather than being concerned with the current location, surgery on the skeleton usually consists of placing hardware through bones, taking a biopsy through the bone, or removing fragments. Therefore, the instrumentation has to be specialized for this application.

Figure 8:
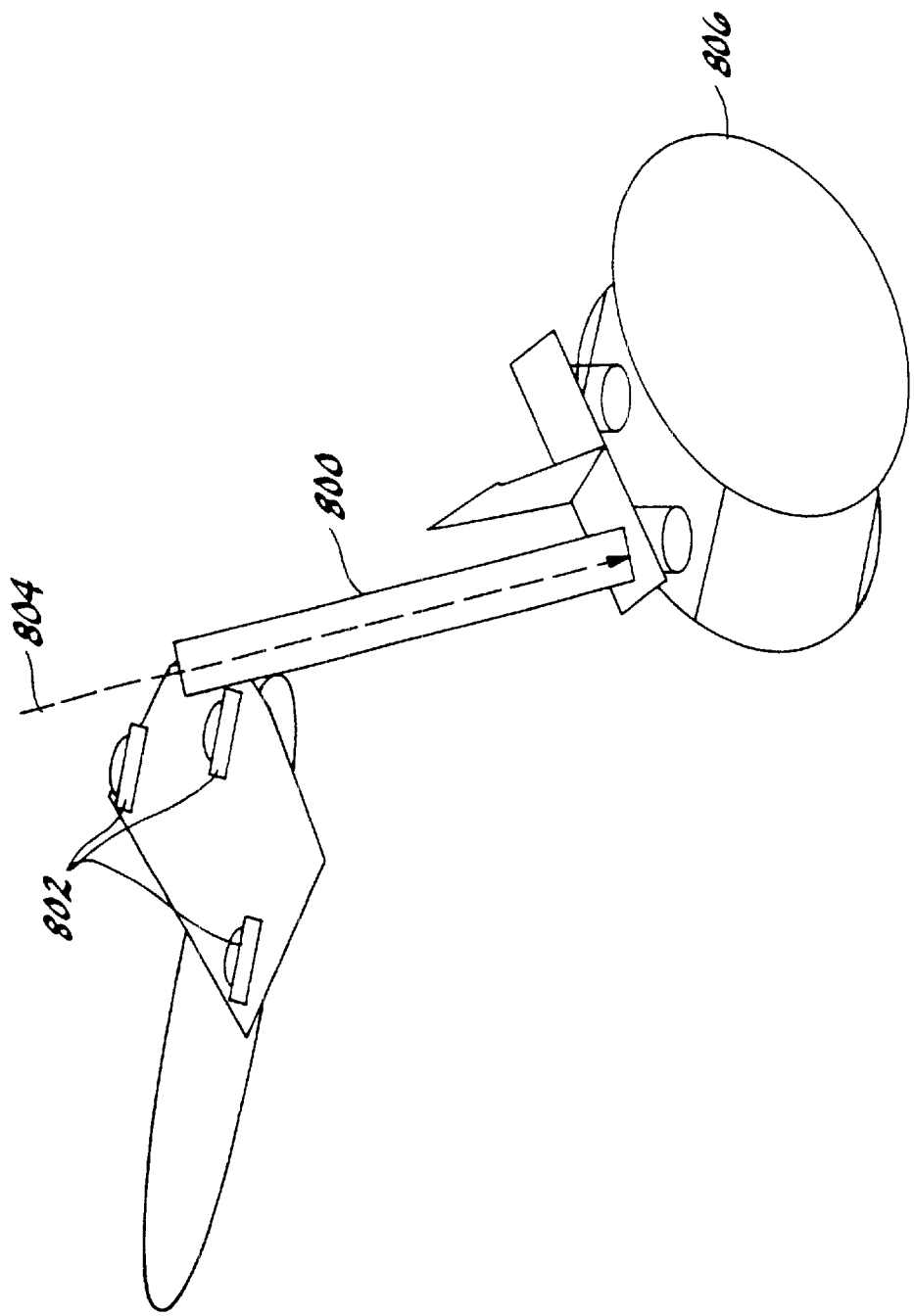
FIG. 8 is an illustration of a drill guide instrument of the invention wherein the position of a drill guide relative to the body elements may be displayed.

One instrument that is used commonly is a drill. By placing emitters on a surgical drill, and by having a fixed relationship between the drill body and its tip (usually a drill bit), the direction and position of the drill bit can be determined. At least three emitters would be needed on the drill, as most drills have a complex three-dimensional shape. Alternatively, emitters could be placed on a drill guide tube 800 having emitters 802, and the direction 804 of the screw being placed or hole being made could be determined by the digitizer and indicated on the image data set (see FIG. 8). The skeletal element 806 would also have emitters thereon to indicate its position.

Besides modification of existing instrumentation, new instrumentation is required to provide a reference system for surgery as discussed above. These reference frames, each equipped with at least 3 emitters, require fixation to the bone which prevents movement or rotation.

Figure 9:
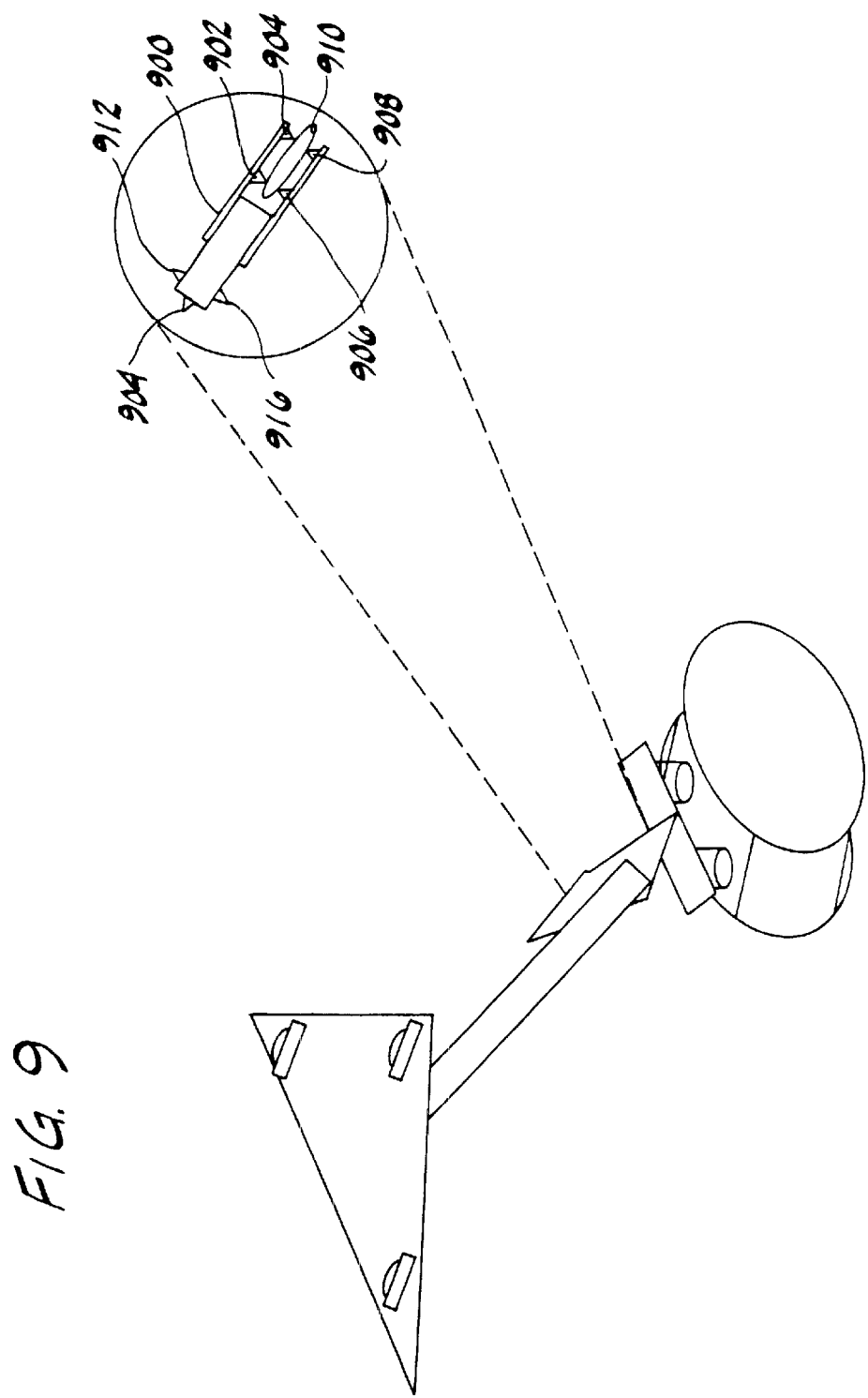
FIGS. 9 and 10 illustrate a clamped reference frame and a wired reference frame, respectively.

For open surgery, a clamp like arrangement, as depicted in FIG. 9, can be used. A clamp 900 is equipped with at least two points 902, 904, 906, 908 which provide fixation to a projection 910 of a skeletal element. By using at least two point fixation the clamp 900, which functions as a reference frame, will not rotate with respect to the skeletal element. The clamp includes emitters 912, 914, 916 which communicate with the array to indicate the position of the skeletal element as it is moved during the procedure.

Figure 10:
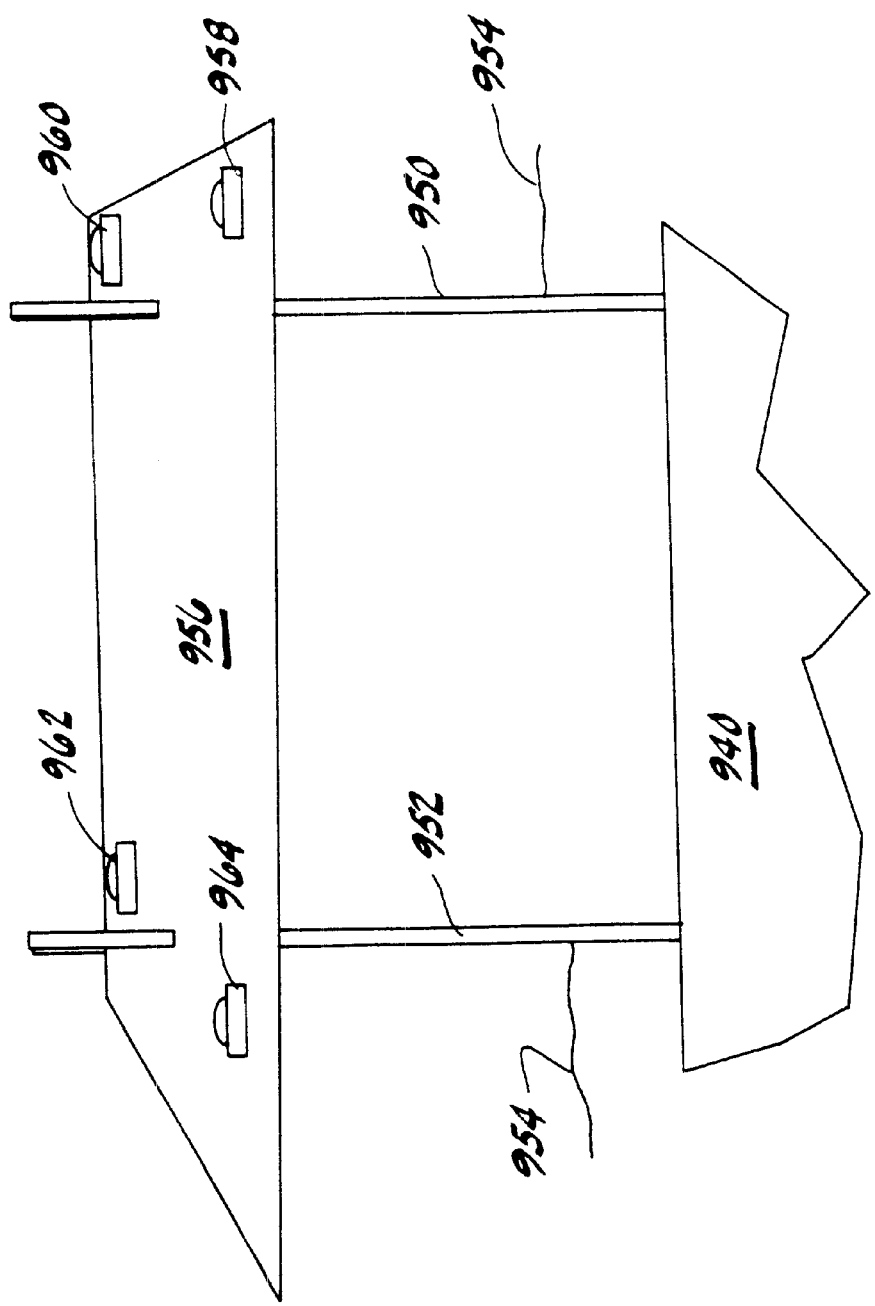

Many procedures deal with bone fragments 940 which are not exposed during surgery, but simply fixated with either wires or screws 950, 952 introduced through the skin 954. FIG. 10 depicts a reference platform 956 attached to such wires or screws 950, 952 projecting through the skin 954. The platform 956 includes a plurality of emitters 958, 960, 962, 964 which communicate with the array to indicate the position of the bone fragment 940 as it is moved during the procedure.

The reference frame can be slipped over or attached to the projecting screws or wires to establish a reference system. Alternatively, the frame can be attached to only one wire, as long as the method of attachment of the frame to the screw or wire prevents rotation, and that the wire or screw cannot rotate within the attached skeletal element.

In view of the above, it will be seen that the several objects of the invention are achieved and other advantageous results attained.

As various changes could be made in the above without departing from the scope of the invention, it is intended that all matter contained in the above description and shown in the accompanying drawings shall be interpreted as illustrative and not in a limiting sense.

What is claimed is:

1. A system for displaying relative positions of body elements during a procedure on a body, the system comprising:

a memory storing an image data set, the image data set representing the position of the body elements based on scans of the body, and having a plurality of data points correlatable to a plurality of reference points for each of the body elements, the position of reference points of a particular body element relative to the data points for that particular body element being known;

a reference system for identifying, during the procedure, the position of the reference points of each of the body elements relative to the reference points of the other body elements;

a processor modifying the spatial relation of the data points of one body element relative to the data points of another body elements according to the identified relative position of the reference points during the procedure as identified by the reference system, the processor generating a displaced image data set representing the position of the body elements during the procedure; and a display utilizing the displaced image data set generated by the processor to display the relative position of the body elements during the procedure.

2. The system of claim 1, wherein the reference system comprises a reference frame in communication with a reference array.

3. The system of claim 2, wherein the reference system determines an orientation of a medical instrument relative to the body elements and the display illustrates the orientation of the medical instrument relative to the body elements.

4. The system of claim 2, further comprising a localizer for determining the position of the reference points of the body elements relative to the reference array.

5. The system of claim 4, further comprising a registration probe in communication with the reference array, wherein the localizer determines the position of a tip of the registration probe relative to the reference array and the position of the reference points of the body elements can be determined by positioning the tip of the registration probe at each of the reference points.

6. The system of claim 4, further comprising a fluoroscopic device for determining a position of a projection of each of the body elements during the procedure,
wherein the processor compares the position of the projection of the each of the body elements during the procedure to the position of the projection of each of the body elements prior to the procedure.

7. The system of claim 6, wherein the fluoroscopic device comprises a fluoroscopic tube in fixed relation to a fluoroscopic plate between which the body elements are located.

8. The system of claim 2, wherein the position of the reference frame is known in relation to one of the body elements, and the reference system determines the position of the reference frame relative to the reference array so that the body may be moved during the procedure while the body elements remain in fixed relation to each other and in known relation to the reference frame so that the system can determine the position of each of the body elements after movement without re-identifying the relative position of each of the reference points of each of the body elements.

9. The system of claim 1, further comprising a medical instrument,
wherein the reference system identifies, during the procedure, the position of medical instrument relative to at least one of the body elements, and the display illustrates the position of the medical instrument relative to the body elements based on the identified position of the medical instrument.

10. The system of claim 1, further comprising a processor for discriminating the body elements of the image data set by creating an image data subset defining each of the body elements.

11. The system of claim 10, wherein the processor translates each of the image data subsets from the position of the body elements prior to the procedure to the position of the body elements during the procedure so that the displaced data set consists of the translated image data subsets.

12. The system of claim 1, wherein the reference system determines a position of a contour of each of the body elements during the procedure and wherein the processor compares the position of the contour of each of the body elements during the procedure as determined by a device to the position of the contour of each of the body elements as represented by the image data set.

13. The system of claim 12, wherein the device comprises an ultrasound probe.

14. The system of claim 12, wherein the device comprises a scanner.

15. A system for displaying relative positions of a plurality of body elements during a procedure on a body, the system comprising:
a memory storing a scan image data set representing the position of the plurality of body elements and having a plurality of data points corresponding to a plurality of reference points for each of the body elements, the position of the reference points of a particular body element relative to the data points for that body element being known;
a plurality of reference frames, each of the plurality of reference frames being configured to be fixed in relation to a separate body element and being correlatable to the position of the reference points for each body element;
a reference array, the plurality of reference frames being in communications with the reference array;
a processor determining the position of the reference points of each body element relative to the other body elements, modifying the spatial relationship of the data points of one body element relative to the data points of another body element according to the relative position of the reference points during the procedure as communicated by the reference frames to the reference array, and generating a displaced image data set representing the position of the body elements during the procedure; and
a display for displaying the position of the body elements during the procedure.

16. The system of claim 15, further including a medical instrument in communication with the reference array, wherein the processor identifies during the procedure the position of the medical instrument relative to at least one of the body elements.

17. The system of claim 16, wherein said display is configured to display the position of the body elements during the procedure and the position of the medical instrument relative to at least one body element.

18. The system of claim 15, wherein the processor discriminates the contour of the body elements of the image data set and creates an image data subset defining each of the body elements.

19. The system of claim 18, further including a scanner for determining the contour of each of the body elements during the procedure, wherein the processor compares the position of the contour of each of the body elements during the procedure as determined by the scanner to the position of the contour of each of the body elements as represented by the image data subset.

20. The system of claim 19, wherein the scanner determines a two-dimensional contour of each of the body elements.

21. The system of claim 19, wherein the scanner determines a three-dimensional contour of each of the body elements.

22. The system of claim 19, wherein the scanner is a scanning probe in communication with the reference array.

23. A method for displaying the relative positions of a plurality of body elements during a procedure on a body, the method comprising:
storing scan images of body elements, the scan images having a plurality of data points corresponding to a plurality of reference points for each of the body elements, the position of the reference points of a particular body element relative to the data points for that particular body element being known;

identifying the position of each of the reference points of each of the body elements relative to the reference points of the other body elements during a procedure;

modifying the spatial relation of the data points of one body element relative to the data points of another body element according to the identified relative position of the reference points during the procedure;

generating a displaced image data set representing the position of the body elements during the procedure; and displaying the relative position of the body elements during the procedure.

24. The method of claim 23, further comprising discriminating the contour of the body elements of the image data set and creating an image data subset defining each of the body elements.

25. The method of claim 24, further comprising scanning the body elements during the procedure to determine the contour of the body elements and comparing the position of the contour of each of the body elements during the procedure to the position of the contour of each of the body elements as represented by the image data subset.

* * * * *